(12) United States Patent
Blue et al.

(10) Patent No.: US 6,470,885 B1
(45) Date of Patent: Oct. 29, 2002

(54) METHOD AND APPARATUS FOR PROVIDING AND CONTROLLING OXYGEN SUPPLY

(76) Inventors: Brent Blue, P.O. Box 3370, Jackson, WY (US) 83014; Steven M. Stokes, P.O. Box 7470, Jackson, WY (US) 83002

( * ) Notice: Subject to any disclaimer, the term of this patent is extended or adjusted under 35 U.S.C. 154(b) by 0 days.

(21) Appl. No.: 09/482,823

(22) Filed: Jan. 13, 2000

(51) Int. Cl.$^7$ .................. A61M 16/00; A62B 7/00
(52) U.S. Cl. ................. 128/204.18; 128/204.24
(58) Field of Search ............... 128/204.18, 204.21, 128/204.22, 204.23, 204.24

(56) References Cited

U.S. PATENT DOCUMENTS

| | | | |
|---|---|---|---|
| 2,414,747 A | 1/1947 | Kirschbaum | |
| 4,336,590 A | * 6/1982 | Jacq et al. | 364/418 |
| 4,584,996 A | * 4/1986 | Blum | 128/204.21 |
| 4,784,130 A | * 11/1988 | Kenyon et al. | 128/204.21 |
| 4,889,116 A | 12/1989 | Taube | |
| 4,971,049 A | * 11/1990 | Rotariu et al. | 128/204.21 |
| 4,972,842 A | * 11/1990 | Korten et al. | 128/716 |
| 5,048,515 A | 9/1991 | Sanso | |
| 5,103,814 A | 4/1992 | Maher | |
| 5,365,922 A | 11/1994 | Raemer | |
| 5,388,575 A | * 2/1995 | Taube | 128/204.23 |
| 5,429,123 A | * 7/1995 | Shaffer et al. | 128/204.23 |
| 5,490,502 A | * 2/1996 | Rapoport et al. | 128/204.23 |
| 5,546,933 A | * 8/1996 | Rapoport et al. | 128/204.23 |
| 5,558,086 A | 9/1996 | Smith et al. | |
| 5,626,131 A | 5/1997 | Chua et al. | |
| 5,664,562 A | 9/1997 | Bourdon | |
| 5,813,399 A | 9/1998 | Isaza et al. | |
| 5,848,591 A | 12/1998 | Weismann | |
| 5,865,174 A | 2/1999 | Kloeppel | |
| 5,934,277 A | 8/1999 | Mortz | |
| 5,954,050 A | * 9/1999 | Christopher | 128/204.23 |
| 6,142,149 A | 11/2000 | Steen | |
| 6,186,142 B1 | * 2/2001 | Schmidt et al. | 128/204.23 |

* cited by examiner

*Primary Examiner*—Dennis Ruhl
*Assistant Examiner*—Darwin P. Erezo
(74) *Attorney, Agent, or Firm*—Weide & Miller, Ltd.

(57) ABSTRACT

A method and apparatus for controlling oxygen delivery to a person is disclosed. In one embodiment, the method includes receiving a goal blood-oxygen saturation level, measuring an actual saturation level of the person, determining a breath rate of the person, sensing a period of inhalation by the person, and delivering oxygen during inhalation by moving a valve to an oxygen delivery position for a calculated period of time based upon the actual saturation level as compared to the goal level of the person's blood-oxygen content. One embodiment of an apparatus comprises an open-loop breathing system including a control valve for controlling the flow of oxygen from a source to the person, a pressure sensor for detecting a period of inhalation, an oximeter for measuring actual blood-oxygen saturation, and a processor for calculating the time the valve needs to be maintained in an open position to deliver oxygen.

7 Claims, 3 Drawing Sheets

METHOD AND APPARATUS FOR PROVIDING AND CONTROLLING OXYGEN SUPPLY

FIELD OF THE INVENTION

The present invention relates to a method and apparatus for controlling a supply of oxygen delivered to a human.

BACKGROUND OF THE INVENTION

There are many instances in which it is desirable, if not necessary, to deliver oxygen to a human. Many of such instances include that where supplemental oxygen is necessary due to medical exigency. Other instances include that where a human is subject to breathing oxygen-depleted air, such as when flying or mountain climbing at high altitudes.

There are a variety of systems for delivering oxygen to a human. Many of the systems are of the so-called "closed loop" breathing systems. In closed-loop breathing systems, the gas which a user breathes is entirely supplied to the user through the system, the user not breathing any gas directly from the atmosphere. Such systems include ventilators.

On the other hand, there are systems of the so-called "open-loop" breathing system. In such systems, a portion of the gas which a user breathes is obtained directly from the atmosphere, and the remaining portion is supplied to the user. These systems have the advantage of generally being less complicated than closed-loop breathing systems, both when considering the apparatus and the control strategy. In particular, an open-loop breathing system may comprise as little as an oxygen supply. The simplicity of the open-loop breathing system makes the system especially desirable for use in situations where space and weight are significant factors, such as in aviation and mountain climbing.

Nonetheless, current open-loop breathing systems suffer from numerous drawbacks. Given the weight and space constraints of aviation and similar environments, it is critical to control the oxygen delivery to the user so that the oxygen which is delivered is used by the user, and is necessary for use by the user. For example, in an open-loop system, oxygen may be delivered to the user continuously, whether or not the user has a need for it from a blood-oxygen standpoint, and whether or not the user is breathing at the time the oxygen is being delivered. This wastes oxygen, making it necessary to provide a much greater oxygen supply than the user actually needs. Providing additional tanks of oxygen adds weight and occupies additional space.

Several schemes have been proposed for controlling oxygen delivery. One early system is that described in U.S. Pat. No. 2,414,747 to Kirschbaum. This patent contains a disclosure of a system in which a person's blood-oxygen level is monitored to control an oxygen supply. The device described therein is quite rudimentary, however, and suffers from a number of drawbacks. A first problem is that the device uses a mechanically complex motor drive arrangement for controlling the flow of oxygen. This drive makes the device large and heavy. In addition, the system does not address the needs of the user when considering the range of blood-saturation levels and breathing patterns.

Other more complex systems have been proposed. For example, U.S. Pat. No. 5,365,922 to Raemer discloses an oxygen saturation control system. As described therein, this system is for use in a closed-loop breathing system employing a ventilator. This system is overly complex because of its application to the closed-loop breathing system, as it will be appreciated that in such systems, great care must be taken to ensure that the fraction amount of oxygen delivered to the patient to prevent oxygen overdose/underdose. This is especially the case in a closed-loop breathing system since the only oxygen which is delivered to the patient is through the system (i.e. the oxygen is not supplemental to that of normal atmospheric breathing, as in the case of an open-loop system). In the arrangement described, "pseudo" blood-saturation signals are generated and a control responsive to the pseudo signal sets a fraction amount of oxygen delivered to the patient.

An oxygen delivery control in an "open"-loop type breathing system which overcomes the above-stated problems is desired.

SUMMARY OF THE INVENTION

The present invention comprises an oxygen delivery control apparatus and method.

In one embodiment of the invention, the oxygen delivery control apparatus is arranged to control the flow of oxygen to a user in an open-loop breathing system including an oxygen supply and a delivery apparatus for delivering supplemental oxygen to a user. In one embodiment, this apparatus comprises a valve provided along an oxygen delivery path between the oxygen supply and the delivery apparatus, the valve having a first position permitting oxygen to flow from the supply to the delivery apparatus, and a second position preventing oxygen from flowing from the supply to the delivery apparatus; a pressure sensor associated with the valve and arranged to detect a period of inhalation by the user by detecting a condition of reduced pressure associated with the apparatus for delivering supplemental oxygen to a user; an oximeter arranged to measure a blood-oxygen saturation level of a user and provide an output signal indicative of the same; and a processor for controlling the valve so as to cause the valve to move to the first position and cause oxygen to be delivered to the user when the output signal from the oximeter indicates a blood-oxygen saturation which is below a selected blood-oxygen saturation level and a condition of inhalation is detected by the pressure sensor.

One or more embodiments of the invention comprise methods for controlling a supply of oxygen to a user. One embodiment comprises a method of controlling the flow of supplemental oxygen from an oxygen supply to a user through a delivery apparatus in an open-loop breathing system, the delivery apparatus including a valve moveable between a first position permitting oxygen to flow from the supply to the user and a second position for preventing oxygen to flow from the supply to the user, comprising the steps of determining a blood-oxygen saturation level of a user; determining the existence of a condition of inhalation by a user; determining if the user requires supplemental oxygen; in the event the user requires supplemental oxygen, determining a length of time the valve should be moved to the first position in order to deliver a desired quantity of oxygen; moving the valve from the second position to the first position for the length of time; and returning the valve to the first position.

In one or more embodiments, oxygen is delivered to a user in accordance with a specific control strategy. In one embodiment, the control strategy for an apparatus controlling the flow of oxygen from an oxygen supply to a user comprises determining a desired blood-saturation goal level; determining an actual blood-saturation level for the user; determining a minimum blood-saturation level for the user;

providing a maximum amount of oxygen to the user if the goal has not been reached and the current level is below the goal level; providing a maximum amount of oxygen to the user if the goal has been reached but the actual level is below the minimum level; providing an amount of oxygen based on an assigned functional relationship between oxygen amount and blood-oxygen content level if the goal has been reached but the actual level is below the minimum level; and providing at least a minimum amount of oxygen if the actual level is above the goal level.

Further objects, features, and advantages of the present invention over the prior art will become apparent from the detailed description of the drawings which follows, when considered with the attached figures.

DETAILED DESCRIPTION OF THE INVENTION

The invention is a method and apparatus for providing and controlling oxygen delivery. In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

Control Apparatus

Figure 1:
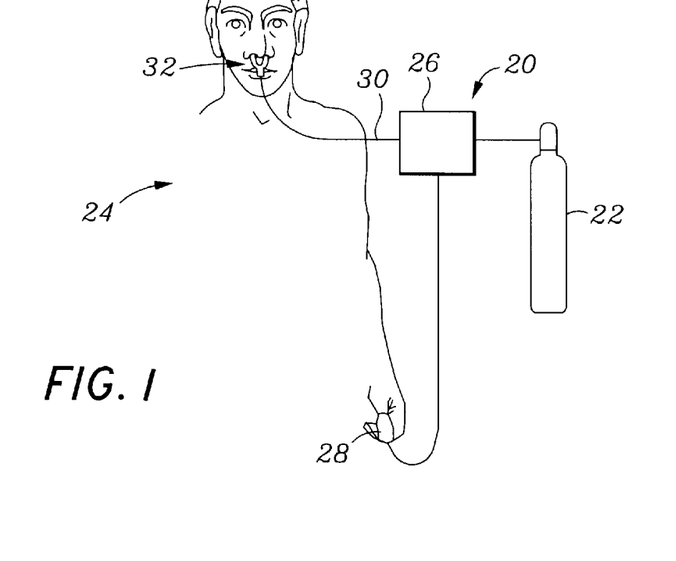
FIG. 1 illustrates a system employing an oxygen delivery control apparatus in accordance with the present invention.

The invention will be described generally first with reference to FIG. 1. As illustrated therein, an oxygen delivery control apparatus 20 is provided for controlling the delivery of oxygen from an oxygen supply 22 to a user 24. The control apparatus 20 includes a controller 26. The controller 26 is arranged to control the flow of oxygen from the supply 22 to the user 24 in a manner causing oxygen to be delivered to a user only when needed, both when considering the blood-oxygen content of the user and the inhalation time(s) of the user.

The oxygen supply 22 may comprise any number of sources for providing oxygen. For example, the supply 22 may comprise a pressurized canister or tank of oxygen. Such supplies are well known and readily available. The particular form of the supply used with the control apparatus 20 of the present invention may depend substantially on the environment of use.

In one arrangement of the invention, the control apparatus 20 is specifically arranged to control the flow of oxygen in an open-loop breathing system. In such a system, the gas which is breathed by the person is at least partially provided directly from the atmosphere, and partially provided from the oxygen supply 22. As illustrated, the oxygen supplied by the oxygen supply 22 is delivered through a delivery tube 30. A delivery end 32 of the delivery tube 30 comprises a nose cannula for delivering oxygen into one or both nostrils of the user 24.

The delivery tube 30 may comprise a flexible clear tubing or other material as well known to those of skill in the art. As will also be appreciated by those of skill in the art, the oxygen may be supplied to a user in other manners. For example, a partial breathing mask or the like may be employed.

The oxygen delivery control apparatus 20 includes means for determining a blood-oxygen content of the user. Preferably, this means is arranged to accurately and continuously determine a person's blood-oxygen content in a non-invasive manner. In a preferred embodiment, this means comprises a pulse-oximeter 28. The pulse oximeter 28 may comprise a so-called "light-beam" type oximeter. The operation and construction of such oximeters are well know and so will not be described in detail here. In general, however, the oximeter 28 is arranged to be worn on a user's finger and provides an analog output signal indicative of the blood-oxygen content of the wearer. It is desirable that the oximeter 28 provide a wide oxygen saturation sensing range (such as 0–100%), work over a wide pulse rate range (such as 18–300 pulses per minute), operate over a wide variety of temperatures and other atmospheric conditions (such as high altitude, high humidity, high or low temperature), be vibration and shock resistant, operate on a minimum voltage supply (such as 2–6 volts DC), and be constructed of biologically (human) compatible material (especially with regard to that portion of the oximeter 28 worn by the user).

It will be appreciated that a number of other devices and methods may be employed for providing the desired blood-oxygen content data. For example, an oximeter of the type worn on the ear-lobe may be employed.

The blood-oxygen content data is supplied to a controller 26. This data may be supplied by a wire or wire-less (such as radio-frequency) connection.

Figure 2:
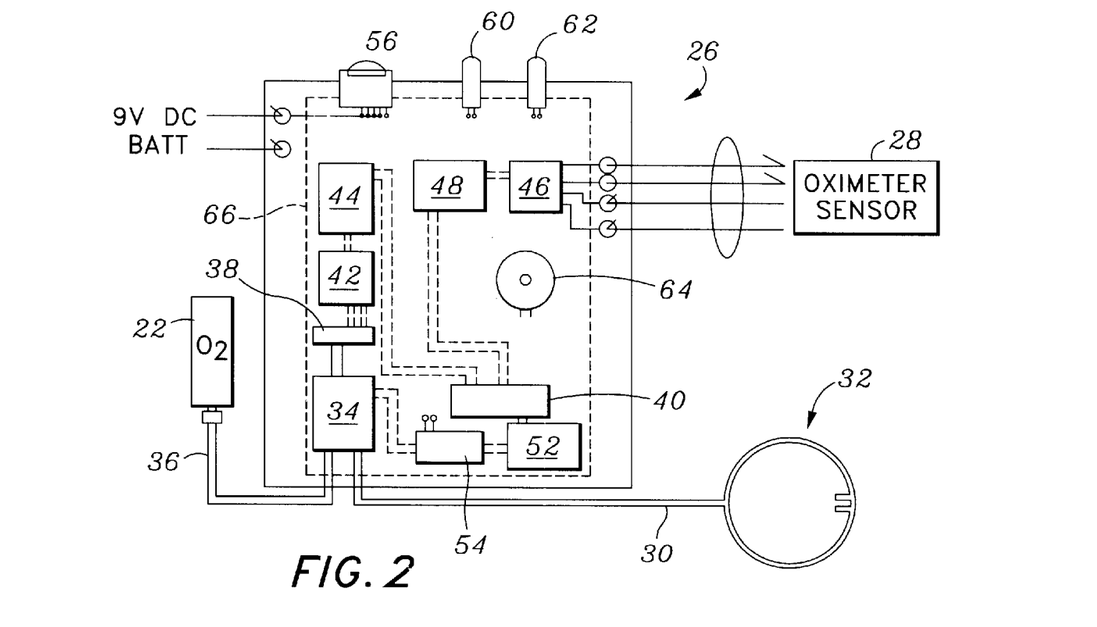
FIG. 2 illustrates in greater detail a controller of the system illustrated in FIG. 1.

The controller 26 will now be described with reference to FIG. 2. The controller 26 includes a means for controlling the flow of oxygen from the supply 22 to the delivery tube 30. In one or more embodiments, this means comprises a valve 34. As illustrated, the valve 34 comprises an electrically operated three-port, solenoid-type valve. The valve 34 has an input to which is connected a supply line 36 leading from the oxygen supply 22. The valve 34 has an output to which is connected the delivery tube 30. As described below, in an embodiment of the invention, a pressure sensor is connected to the third port of the valve 34.

In one or more embodiments, the valve 34 is constructed from brass or a similar biologically (human) compatible material. The valve 34 has a duty cycle of about 6–30 times per minute or more, and is capable of working within the environment of the maximum pressures associated with the apparatus 20. In one embodiment, the solenoid of the valve 34 is activated to move the valve to an "open" or first position upon the application of a relatively low electrical voltage input, such as 5 volts DC. In this arrangement, the valve 34 preferably moves to a second or "closed" position when the activating voltage is removed from the solenoid.

The means for controlling the flow of oxygen may comprise other than the valve described above. For example, the valve 34 may be of a different type and be mechanically operated. The valve 34 may also be arranged to that an electrical signal must be applied to open the valve and another signal applied to close the valve. The valve may comprise a two port valve, though as described in more detail below, the embodiment of the valve 34 described above is advantageous when used in conjunction with a control strategy in which the flow of oxygen in controlled by the time the signal is applied to the valve 34 to maintain it in an open position. In an embodiment where the valve has two ports, a first port may be associated with the oxygen supply, and a second with both the pressure sensor and delivery tube (such as where the pressure sensor and delivery tube are associated with a "T" fitting connected to the second port of the valve).

The controller 26 includes means for sensing a pressure in the delivery tube 30. In one or more embodiments, this means comprises a pressure sensor 38. In one or more embodiments, the pressure sensor 38 is of the diaphragm-type, providing a pressure signal based on the position of the diaphragm.

In one or more embodiments of the invention, the pressure sensor 38 is associated directly with the valve 34. In particular, the pressure sensor 38 is associated with the third port of the three-port valve 34 (or when the valve has two ports, as described above, the second port thereof). In this embodiment valve 34, when the valve is in its first or open position, a pathway is established therethrough from the first port (the port to which the oxygen delivery tube 30 is connected) to the second port (the port to which the delivery tube 30 is connected). In this valve position, the pressure sensor 38 is effectively cut off from the delivery tube 30. When the valve 34 is in its second or closed position, a pathway is established therethrough from the third port (to which the pressure sensor 38 is connected) to the second port (the port to which the delivery tube 30 is connected). In this arrangement, the pressure sensor 38 is arranged to operate and deliver a signal indicative of the pressure in the delivery tube 30 only when the valve 34 is not in its open, oxygen delivery position.

The controller 26 includes a processor 40. The processor 40 provides a processing environment whereby an output is generated in response to an input. In the arrangement illustrated, the input comprises a signal from the pressure sensor 38, as well as a signal from the oximeter 28.

The pressure sensor 38 provides a pressure signal to the processor 40. This signal comprises an electrical voltage representing a specific pressure.

The oximeter 28 provides a signal representing the blood-oxygen content of the wearer to the processor 40. This signal also comprises an electrical voltage, but representative of the blood-oxygen saturation level.

In one or more embodiments, the processor 40 includes a memory on which various data and instructions are stored, and an associated digital signal processor for executing the instructions. In a preferred embodiment, the memory comprises an erasable/programmable read only memory chip (EPROM). The memory may comprise a wide variety of other devices now or later known, such as an electronically erasable programmable read-only chip (EEPROM), Flash ROM or the like. The digital signal processor may be integral with the memory or separate therefrom, and may comprise a wide variety of devices, such as a processor manufactured by the Intel or AMD corporations. The exact nature of the processor 40 may depend on the specific control strategy employed. While the control strategy described below is rather complex, it does not require a processing environment of such high capacity as generally found in desktop and portable computers arranged to perform a wide variety of tasks.

In the arrangement illustrated, the output signal generated by the pressure sensor 38 is an analog signal. Preferably, this signal is amplified by an amplifier 42, and then converted into a digital signal with an analog to digital (A/D) converter 44. It is noted that in the embodiment of the invention illustrated, the processor 40 is arranged to only process the pressure sensor 38 signal during the time the pressure sensor 38 is active, in the sense that it is coupled to the delivery tube 30. This is because at other times, the signal sent by the pressure sensor 38 is not indicative of the pressure in the delivery tube 30, since the pressure sensor 38 is cut off from the delivery tube by the valve 34.

In the arrangement illustrated, the output signal generated by the oximeter 28 is an analog signal. Preferably, this signal is amplified by an amplifier 46, and then converted into a digital signal with an analog to digital (A/D) converter 48.

The processor 40 employs a control strategy for controlling the valve 34. Preferably, this control strategy is as described in detail below, and is based on the input signals from the oximeter 28 and pressure sensor 38. As illustrated, the processor 40 generates an output signal for use in controlling the valve 34. The output signal is converted from a digital to an analog form with a digital to analog (D/A) converter 52. The converted signal then passes through a relay 54 to the valve 34. In this arrangement, the processor 40 is arranged to provide an output signal which, when provided to the valve 34, opens the valve. When the output signal is removed from the valve 34, then the valve 34 closes.

A selector 56 is provided which allows a user to select a desired blood-oxygen content level to be maintained with the apparatus 20. In the embodiment illustrated, the selector 56 comprises a button which the user may push to select incremental blood-oxygen saturation goal level values. In this regard, a small display may be provided for displaying the currently selected goal level. In one or more other embodiments, the selector 56 may comprise a rotatable knob connected to a resistance-type output device which generates an electrical output signal related to the position of the knob. In general, in one or more embodiments, the selector 56 provides an output signal to the processor 40 indicative of the desired blood-oxygen saturation level.

In one or more embodiments, the selector 56 also serves as an ON/OFF switch for the controller 26. The various components of the controller 26 may be powered in a number of manners. As illustrated, the controller 26 is powered by a battery, such as a small nine volt (9V) battery. The ON/OFF function of the selector 56 is arranged to selectively couple and decouple the battery power from the components of the controller 26. It will be appreciated that a separate ON/OFF switch may be provided.

One or more means are provided for indicating to the user the status of the apparatus 20. As illustrated, the means include audible and visible indicators. The visible indicators comprise a green light 60 and a red light 62. The audible indicator comprises a speaker 64. In an embodiment of the invention, the lights 60,62 and speaker 64 are controlled by the processor 40.

In one embodiment, the processor 40 is arranged to cause the red light 62 to illuminate when the controller 26 is powered, but not currently operating "normally." For example, the red light 62 may be illuminated while the processor 40 is in an initialization mode, or when a malfunction has occurred.

In one embodiment, the processor 40 is arranged to cause the green light 60 to illuminate when the controller 26 is operating normally.

In one embodiment, the processor 40 is arranged to cause the speaker 64 to issue an audible alarm in one or more events. Such events may be a malfunction of the device, low battery condition, user breathing problem, or the like.

In a preferred embodiment of the invention, the components of the controller 26 are associated with, and more particularly, mounted on, a circuit board 66. This arrangement permits the controller 26 to be extremely compact. In addition, the connection of the components may be accommodated with a Steiner tree micro connection instead of by a plurality of wires or the like. This renders the controller 26 very durable. In one or more embodiments, the circuit board 66 may have a dimension of approximately 2.5 inches by 3 inches. As may be appreciated, in such an arrangement, the size and weight of the controller 26 are extremely minimal.

Though not illustrated, the controller 26 may be mounted in a housing. The housing may have openings therein through which the lights 60,62 and selector 56 protrude, and including openings for ports through which the supply line 36, delivery line 30, battery wiring and oximeter wiring may pass. The housing may be constructed from a wide variety of materials, and may be constructed to be waterproof, shock-resistant and the like.

Control Strategy

Referring to FIGS. 3(*a*) and (*b*), a method of the invention will now be described. In general, the apparatus 20 of the invention is preferably arranged to maintain a user's blood-oxygen level at a desired level by administering the proper amount of oxygen to the user. Moreover, the apparatus 20 is not only arranged to provide oxygen to the user only at such times as the user needs supplemental oxygen, but only at those times the user is inhaling and the oxygen delivered to the user will actually be utilized. In this manner, oxygen is conserved.

Referring to FIG. 3(*a*), in a step S1, a desired blood-oxygen saturation level is determined. In one or more embodiments, this step comprises the step of the user inputting a desired level to the processor 40 using the selector 56. In one or more other embodiments, the desired level may be input by a party other than the user, such as a medical care provider. The desired level may be input from an external control via a specially configured input, such as from a computer which is programmed by the user or a medical care provider.

Figure 3A:
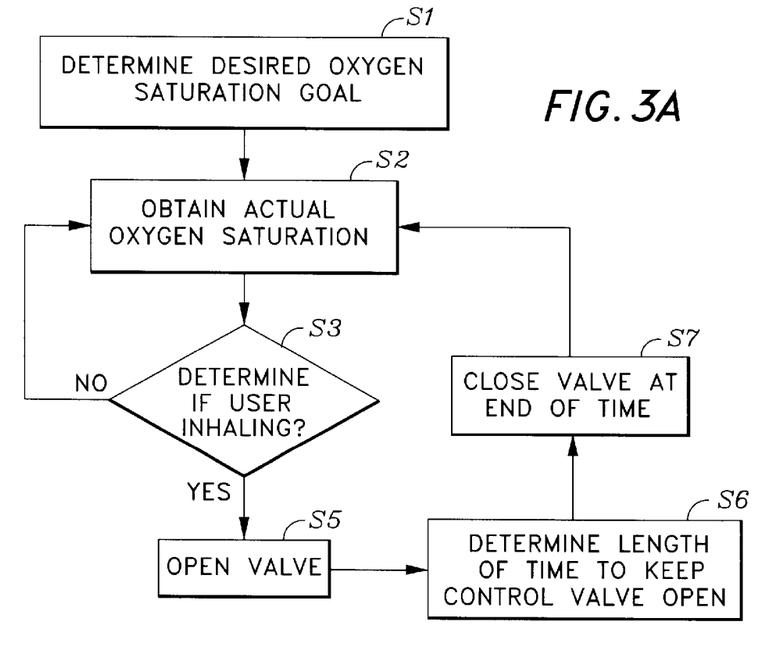
FIG. 3(a) is a flow diagram illustrating a method for providing and controlling oxygen delivery in accordance with the present invention.

In a step S2, the actual blood-oxygen saturation level of the user of the apparatus is determined. In one or more embodiments, this step comprises the step of the oximeter 28 sending to the processor 40 a signal indicative of the measured blood-oxygen level of the user.

In a step S3, it is determined if the user of the apparatus is accepting supplemental oxygen. In one or more embodiments, this step comprises the step of determining if the user is inhaling. This is determined by the pressure sensor 38. When the user begins to inhale, the associated pressure drop is detected by the pressure sensor 38. The pressure sensor 38 sends this signal to the processor 40 representative of the pressure.

In a step S4, if the user is not inhaling, then the method returns to step S2. In other words, no oxygen is delivered to the user when the user is not inhaling. Instead, the blood-oxygen saturation level is updated, and the process returns to step S3.

Figure 3B:
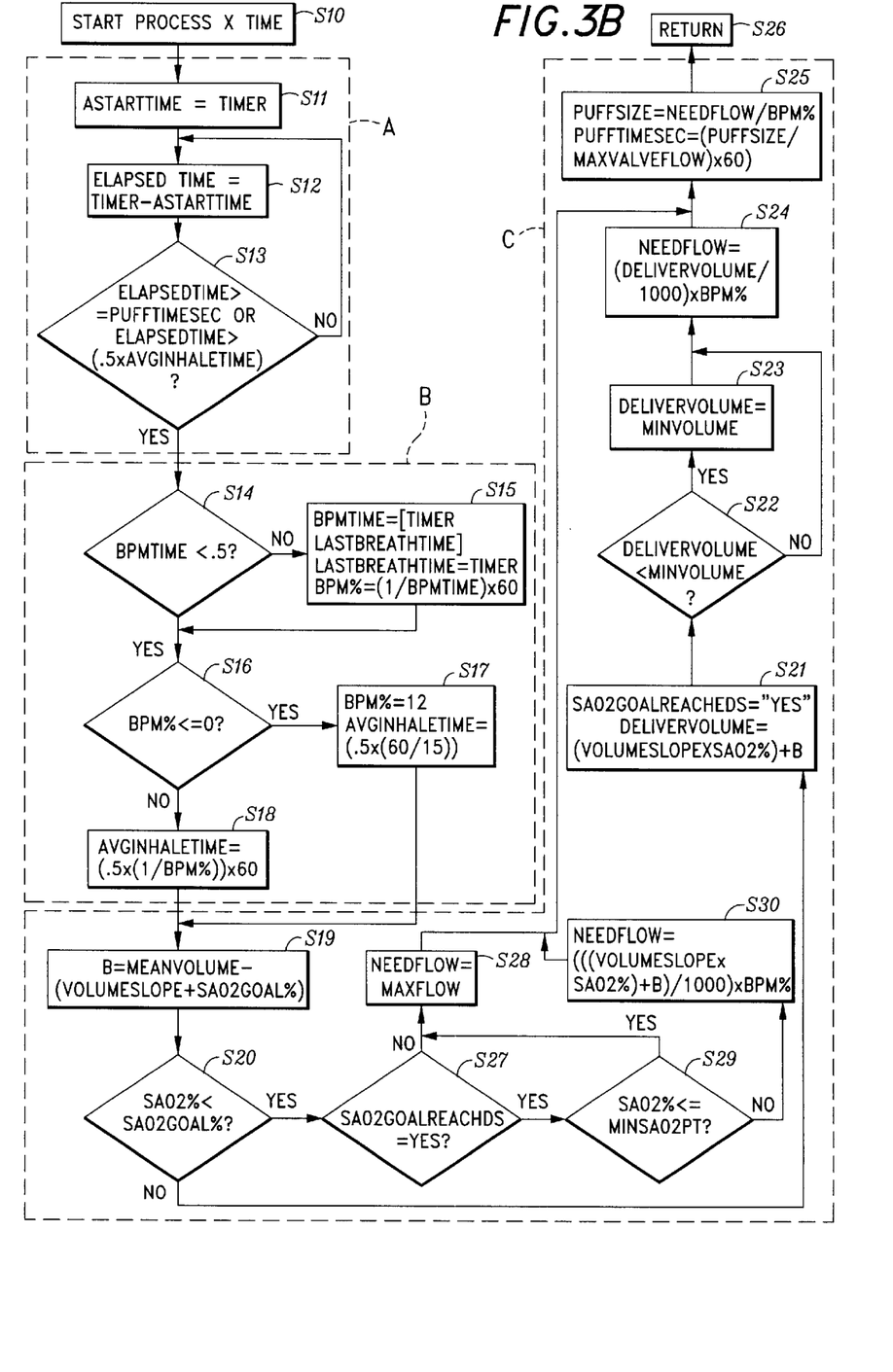
FIG. 3(b) is a flow diagram illustrating a method for determining an oxygen delivery time in accordance with the method illustrated in FIG. 3(a)

If in step S4 it is determined that the user is inhaling, then the process moves to step S5. In step S5, the valve 34 is opened. This permits oxygen to flow from the supply 22 to the user. In a step S6, a length of time that the valve 34 is to be maintained in its open position is determined. This step may be accomplished in a wide variety of manners. A preferred embodiment for accomplishing this step is described in more detail below with reference to FIG. 3(*b*).

Once the length of time for opening the valve 34 has been determined, the valve 34 is maintained in its open position for the determined time, and then in a step S7, closed. In one or more embodiments, the closing of the valve 34 is effectuated by removing the signal from the valve 34 which is causing the valve 34 to remain in its open position.

Thereafter, the process returns to step S2. The blood-oxygen saturation level is updated.

FIG. 3(*b*) is a flow-diagram illustrating a method for determining the length of time the valve 34 should be maintained in its open position. In general, the time which the valve 34 is maintained in its open position is in direct relationship to the amount of oxygen which is to be delivered to the user.

Referring to FIGS. 3(*c*) and 3(*d*), this method employs two control strategies dependent upon the condition of the user. First, as illustrated in FIG. 3(*c*), until a user's blood-oxygen saturation exceeds a desired or goal level, or if the level has fallen below a minimum set level, a maximum flow is provided to the user. Second, as illustrated in FIG. 3(*d*), if a user's blood oxygen saturation has reached the goal once, then (a) if the saturation level has fallen back below the goal (but not below an assigned minimum), then the delivery volume provided to the user is based on a mathematical relation between delivery volume and the blood-oxygen saturation (actual and goal) and (b) if the user's level remains above the goal, then a minimum delivery volume is provided. In FIG. 3(*d*), it is noted that the "y"-axis values correspond to oxygen delivery volume (and not rate).

In one or more embodiments, the mathematical relationship provided in FIG. 3(*d*) is linear. It will be appreciated that the relationship may have other forms, such as exponential, second degree or the like. The linear relationship is satisfactorily accurate and has the advantage of being less complex to process.

In general, the process for determining the length of time the valve 34 is to remain open comprises three main components: (1) a timing sequence for insuring that the signal to the valve 34 for opening it remains active a desired length of time to deliver the desired flow volume; (2) a sequence for determining a breath time for the user; and (3) a sequence for determining a delivery flow volume to be provided to the user based on the breath time and the desired and actual blood-oxygen saturation values for the user.

Referring again to FIG. 3(*b*), an embodiment of a method for determining the valve opening time is disclosed. In a step S10, this process is initiated. In a step S11, a time associated with a timer is determined (AStarttime). In one or more embodiments of the invention, the timer is an internal clock which provides an output of the number of seconds after midnight (or other reference point) when called. The timer may be associated with the processor 40.

In a control loop A of this process, the method or process is maintained in a loop condition until the total elapsed time that the valve 34 has been maintained in its open position is equal to or exceeds a desired time. In one embodiment, the loop A comprises the step S12 of determining an elapsed time. The elapsed time comprises the difference between a new time (as determined from the timer) and the previously determined start time (AStartTime) in step S11. In a step S13, it is determined if this elapsed time either (a) is greater than or equal to a calculated time to maintain the valve open (PuffTime) or (b) greater than half of a determined average inhale time (AvgInhaleTime). In accordance with this logic, it is assumed that the first half of a user's inhalation cycle comprises the main part of the inhalation cycle/volume. Oxygen need not be delivered to the user, even if a calculated flow time exceeds this "half" inhalation cycle time, since the delivered oxygen will be wasted.

If neither condition is satisfied, the loop returns to step S11, thus maintaining the valve 34 open. It is noted that in the arrangement of the process as illustrated, values such as the calculated valve open time may not be determined or stabilized in the first several loops through the process. In such event, the process continues quickly to steps described below in which such times are generated. After one or more iterations through the process (which will generally take only a few seconds) these values will optimize to the user's condition.

If in step S13 either condition is satisfied, then the process moves to a sub-process B where a number of breaths per minute value (BPM%) and the average inhalation time (AvgInhaleTime) of the user is determined. In a step S14, a breaths per minute time (BPMtime) is compared to a value. In this case, the value is 0.5. If the breaths per minute time is greater than the value, then in a step S15, a new breaths per minute time is calculated. In one embodiment, this time comprises a time between a current timer value and a time of the last breath (as indicated by the timer in relation to the pressure sensed inhalation). From this value, a breaths per minute value (BPM%) is determined. This value comprises the value one (1) divided by the breaths per minute time, multiplied by sixty (60).

Once step S15 is completed, or if the breaths per minute time is less than the value in step S14, then in a step S16, the breaths per minute value is compared to zero (0). If the breaths per minute value is less than or equal to zero (0), then in a step S17 the breaths per minute value is set at a predetermined value (generally based on an average breaths per minute value for a human, such as 12). An average inhalation time (AvgInhaleTime) is then calculated. This time is generally equal to half the time of each breath (half of each breath is assumed to be inhalation and half exhalation).

If in step S16 the breaths per minute value (BPM%) is greater than zero (0) (i.e. a reasonable value has already been assigned), then in a step S18, an average inhalation time is calculated based on the breaths per minute value. In one embodiment, the average inhalation time comprises 0.5* (1/breaths per minute value)* 60.

The process then exits sub-process B to a step S19. In accordance with this step, a value is determined in accordance with the relationship set forth in FIG. 3(d). In particular, a value B is determined based on an assigned value for a mean flow volume, less the slope of the flow function multiplied by the user's desired blood-oxygen goal.

The process then enters a sub-process or function C. This function is arranged to determine the next succeeding time duration that the valve 34 is to be maintained in its open condition. In a step S20, the user's current blood-oxygen saturation level (SAO2%) is compared to the user's goal (SAO2goal%). If the actual level is above the goal (answer "N"), then in a step S21 it is known that the goal has been reached. A delivery volume is determined using the function set forth in FIG. 3(d). In this case, the delivery volume is equal to the slope of the function multiplied by the actual blood-oxygen level, plus the value B.

In a step S22 it is determined if the calculated delivery volume is less than a minimum desired delivery volume (MinVolume). If so, then in a step S23, the delivery volume is set to the minimum volume. If not, then it is determined in a step S24 that the needed flow (NeedFlow) is equal to the delivery volume divided by 1000, multiplied by the breaths per minute value (step S16) It is noted that in this step the value (delivery volume/1000) is multiplied by the breaths per minute value because the next step includes a breath per minute value divider. This is necessary as a result of the particular methodology employed in that the value realized from step S28 (described below) is not based on the breaths per minute value. Those of skill in the art will appreciate the numerous arrangements (mathematical and otherwise) for achieving the objectives of the steps described herein.

In a step S25, the size of the delivery volume (PuffSize) is determined. This volume comprises the needed flow amount divided by the breaths per minute value. Once this value is known, the amount of time for which the valve 34 must be maintained in its open position to provide the desired volume is determined. This time, the PuffTime, comprises the delivery volume (PuffSize) divided by the maximum flow rate associated with the valve 34, multiplied by sixty (60).

In a step S26, the process returns to the main process, as at step S7 of FIG. 3(b). At that point, the valve 34 is closed, stopping the flow of oxygen.

Figure 3C:
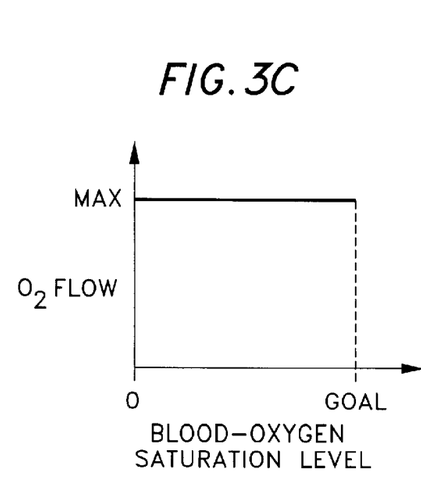
FIG. 3(c) is a graph illustrating a first relationship between a user's blood-oxygen saturation level and an oxygen flow rate for use in determining the delivery time in accordance with the method illustrated in FIG. 3(b)

If in step S20 it is determined that the user's actual blood-oxygen level is below the goal, then it is determined in a step S27 if the user's actual level ever exceeded the goal. If not, then the control strategy illustrated in FIG. 3(c) is employed: in a step S28, the flow which is needed by the user is set to the maximum flow value (MaxFlow). In a step S25, the time which the valve 34 must remain open to provide this flow is then calculated.

If in step S27 it is determined that the goal has been reached at some point, then it is determined in step S29 if the user's actual blood-oxygen saturation level is below a minimum value. If so, then the needed flow is set to the maximum flow via step S28.

Figure 3D:
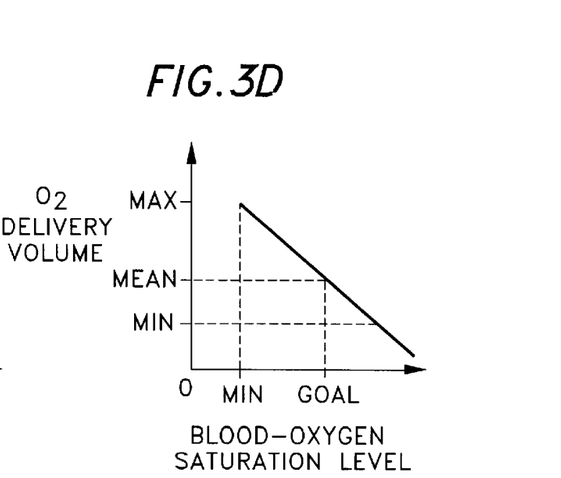
FIG. 3(d) is a graph illustrating a second relationship between a user's blood-oxygen saturation level and an oxygen delivery volume for use in determining the delivery time in accordance with the method illustrated in FIG. 3(b).

If in step S29 it is determined that the user's actual blood-oxygen level is greater than the minimum level, the in a step S30, the needed flow is determined in accordance with the relationship set forth in FIG. 3(d): the needed flow is determined from the slope of the function multiplied by the actual saturation value (SAO2%), plus the value B, then divided by 1000, and then multiplied by the breaths per minute value. Then in step S25 the time for which the valve 34 must be maintained open is determined.

It will be seen that in the above-described embodiment, the valve 34 is maintained in an open position for at least as long as a calculated time (pufftime) or half of an average inhalation time. Again, it has been found that most of the inhaled volume occurs during only half of a user's inhalation cycle. Therefore, it is wasteful to deliver oxygen for greater than this period of time. In the above-described arrangement, a calculated time is provided for optimizing the delivery volume. In some instances, however, this delivery time may exceed half of the user's inhalation cycle. In such event, it is desirable to limit the delivery time to half of the user's inhalation cycle.

In one or more embodiments, the value of "half" or "0.5" of the average inhalation time may be varied (as in steps S13, S17, etc.). For example, a value of 0.3–0.4 or less, or 0.6–0.7 or more may be found to more useful in controlling the oxygen delivery in one or more situations. In addition, the exact percentage of the inhalation time which is used in the method may be varied dependent upon a number of conditions.

Those of skill in the art will appreciate that there are a variety of manners for accomplishing the above-described effect. For example, it is noted that the processes and sub-processes can be rearranged in a variety of orders and be determined in accordance with a wide variety of calculations. As described above, in one or more embodiments, the relationship between delivery volume and blood-oxygen saturation level may be other than linear (referring to FIG. 3(d)). In such event, the calculations in steps S19, S21, and S30 may vary dependent upon the exact relationship used. For example, a second degree relationship of the form $y=ax^2+bx+c$ may form the relationship.

Use of Apparatus

Use of the apparatus 20 of the invention is as follows. First, a user connects an appropriate supply of oxygen 32 to the apparatus 20.

The user positions the oximeter 28 appropriately. For example, if the oximeter 28 is of the type which is to be worn on a finger, the user places the oximeter 28 on a finger.

The user positions the delivery end 32 of the delivery tube 30 or other delivery device. In the case of the delivery tube 30 as illustrated, the tube is placed by the user in the nostrils.

Next, the user activates the controller 26. In the embodiment described above, this comprises the user turning on the controller 26 with the selector 56. In the embodiment of the apparatus 20 described above, the red light 62 will illuminate for a short time during the initialization process of the processor 40. Thereafter, the processor 40 causes the green light 60 to illuminate. This indicates to the user that the controller 26 is ready for operation.

The user then selects the desired blood-oxygen saturation level to be maintained. This comprises selecting the level with the selector 56. As provided above, the manner by which this is accomplished may depend on the type of selector 56.

Thereafter, the controller 26 causes oxygen to be delivered to the user. As described above, the apparatus 20 is arranged so that oxygen is delivered to the user in short bursts during the inhalation cycle of the user. The amount of oxygen delivered is controlled (by the duration of delivery) so that the blood-oxygen saturation level is maintained.

Advantageously, the control strategy of the invention causes a maximum oxygen delivery rate to be employed if the user's blood-oxygen saturation level is below the desired or selected level, or if below a pre-set minimum value. This arrangement effectuates a rise in the user's blood-oxygen saturation level as fast as possible. For example, if a user has a very low blood-oxygen saturation level, such as in an emergency or other critical situation, the apparatus 20 is arranged to automatically deliver maximum oxygen to the user. As may be appreciated, a condition of oxygen deficiency, a user might not be able to make the decisions necessary to operate a complicated control. In accordance with the invention, this is avoided.

On the other hand, once a user's blood-oxygen saturation goal has been met, and so long as it does not fall below a minimum value, the flow rate to the user is chosen in a manner which maintains the user's blood-oxygen saturation level and yet does not over-supply oxygen. This reduces the oxygen waste and improves user comfort.

An advantage is realized by the arrangement of the pressure sensor 38 and valve 34. In particular, the pressure sensor 38 only needs to be used to differentiate a static pressure in the delivery tube 30 from an inhalation pressure (drop). This is because the pressure sensor 38 is only in communication with the delivery tube 30 when no oxygen is being delivered. If the pressure sensor 38 were always in communication with the delivery tube, the pressure drop at the end of the oxygen delivery cycle would have to be differentiated from the pressure drop at the beginning of inhalation by the user, as in a arrangement where a two-port valve is employed (for example, when a two-port valve is employed, the processor may need to be arranged to ignore pressure signals when the system is over-charged or pressurized with oxygen).

The apparatus 20 and method of the invention has numerous other advantages. One advantage is that the construction and arrangement of the apparatus 20 is its lightweight and small design.

Another advantage of the particular arrangement of the apparatus 20 described above is that both sides of a diaphragm of the pressure sensor 38 are open or exposed to the ambient atmosphere. In such an arrangement, the apparatus 20 is "self-correcting" for altitude. In other words, the changes in altitude do not affect the accuracy of the pressure sensor 38. This is important since a variety of uses of the apparatus 20 are at high altitudes, such as mountain climbing and flying.

It will be understood that the above described arrangements of apparatus and the method therefrom are merely illustrative of applications of the principles of this invention and many other embodiments and modifications may be made without departing from the spirit and scope of the invention as defined in the claims.

We claim:

1. A method of controlling a flow of supplemental oxygen from an oxygen supply to a user through a delivery apparatus in an open-loop breathing system, the delivery apparatus including a valve moveable between a first position permitting oxygen to flow from said supply to said user and a second position for preventing oxygen to flow from said supply to said user, comprising the steps of:

receiving a goal blood-oxygen saturation level of a user;

determining an actual blood-oxygen saturation level of a user;

determining a breath rate of said user;

sensing periods of inhalation by said user;

determining a length of time said valve should be moved to said first position in order to deliver a desired quantity of oxygen, said determining step comprising determining a first maximum time if said actual level has not reached said goal level or said actual level is below a minimum level, determining a second minimum time if said actual level is above said goal level, and determining a variable time if said actual level has at least once reached said goal level but said actual level is between said minimum level and said goal level, said step of determining a variable time including determining a breath rate of said user from said sensed periods of inhalation by said user, determining a delivery volume comprising a desired quantity of oxygen divided by said breath rate, and determining said variable time by dividing said delivery volume by a flow rate of supplemental oxygen available;

detecting the initiation of inhalation by said user; and moving said valve from said second position to said first position for said determined length of time; and returning said valve to said first position.

2. The method in accordance with claim 1 wherein said step of determining a blood oxygen saturation level comprises measuring a blood-oxygen saturation level of said user with a pulse-oximeter.

3. The method in accordance with claim 1 wherein said step of determining the initiation of inhalation by a user comprises sensing a drop in pressure at said delivery apparatus.

4. The method in accordance with claim 1 wherein said desired quantity of oxygen comprises a maximum quantity when said actual level is below said minimum level.

5. The method in accordance with claim 1 wherein said desired quantity of oxygen comprises a linearly changing quantity between a minimum quantity corresponding to said minimum time and a maximum quantity corresponding to said maximum time.

6. The method in accordance with claim 1 wherein said step of moving said valve comprises applying a signal to said valve causing said valve to be retained in its first position for said determined length of time.

7. The method in accordance with claim 1 wherein said determined length of time does not exceed one-half of an inhalation time of said user.

* * * * *